United States Patent [19]

Robinson

[11] 4,047,100
[45] Sept. 6, 1977

[54] METER FOR MEASURING SYRUP RATIO IN SOFT DRINKS AND THE LIKE

[75] Inventor: Myron L. Robinson, Solana Beach, Calif.

[73] Assignee: Simekus, Inc., Vista, Calif.

[21] Appl. No.: 676,566

[22] Filed: Apr. 13, 1976

[51] Int. Cl.² .............................................. G01N 27/42
[52] U.S. Cl. .................................... 324/30 B; 324/29
[58] Field of Search .................... 324/29, 30 R, 30 B, 324/DIG. 1; 204/195 R, 195 F

[56] References Cited

U.S. PATENT DOCUMENTS

| 2,837,271 | 6/1958 | Haglund | 324/30 B |
| 2,922,103 | 1/1960 | Smith | 324/30 B |
| 3,512,080 | 5/1970 | Hanson | 324/30 B |
| 3,664,306 | 5/1972 | Quayle | 324/30 B |

Primary Examiner—Rudolph V. Rolinec
Assistant Examiner—Michael J. Tokar
Attorney, Agent, or Firm—Harris, Kern, Wallen & Tinsley

[57] ABSTRACT

Method and apparatus for measuring the conductivity ratio of a sample for determining deviation from a standard and particularly suited for use in measuring the syrup to water ratio in soft drinks and the like. A pair of conductivity cells for receiving the standard and sample, with the cells connected in a bridge circuit operated at relatively high frequency and having a full wave recitifier at the bridge output providing an input to an operational amplifier for driving an indicating meter which can be read in percent deviation from the standard. A side by side cell mounting with electrodes in the lower cell sections and a metal heat exchanger forming the upper cell sections. A pair of plungers for insertion into the cells for equalizing the amounts of material in the cells and the temperature of the materials. A calibration procedure for adapting the instrument for use with various products.

12 Claims, 7 Drawing Figures

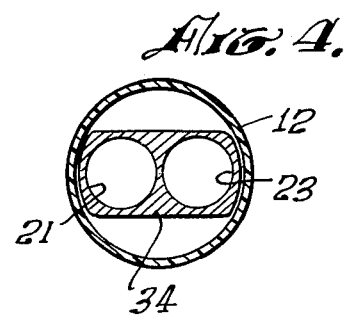
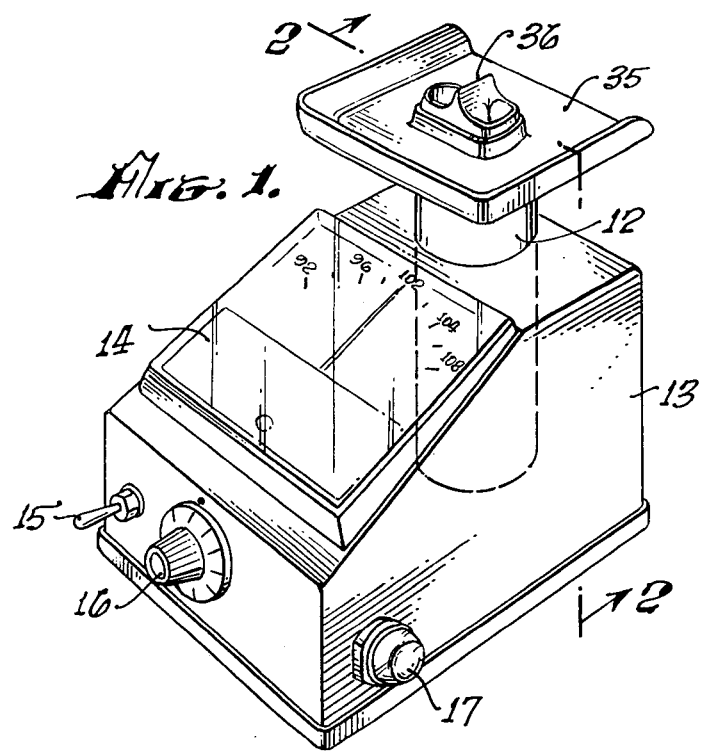
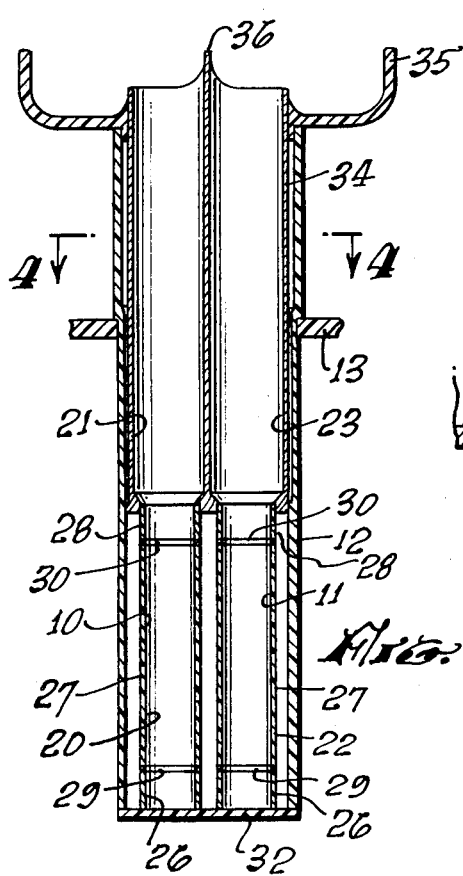
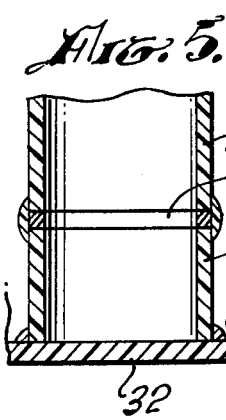
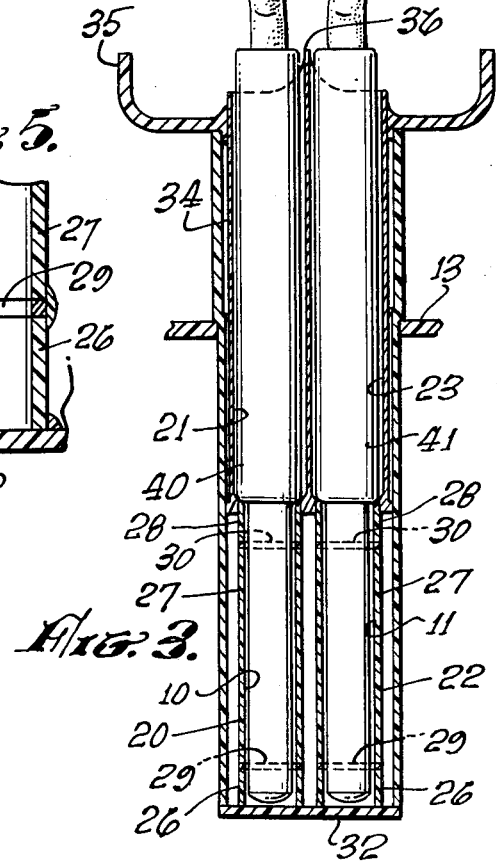

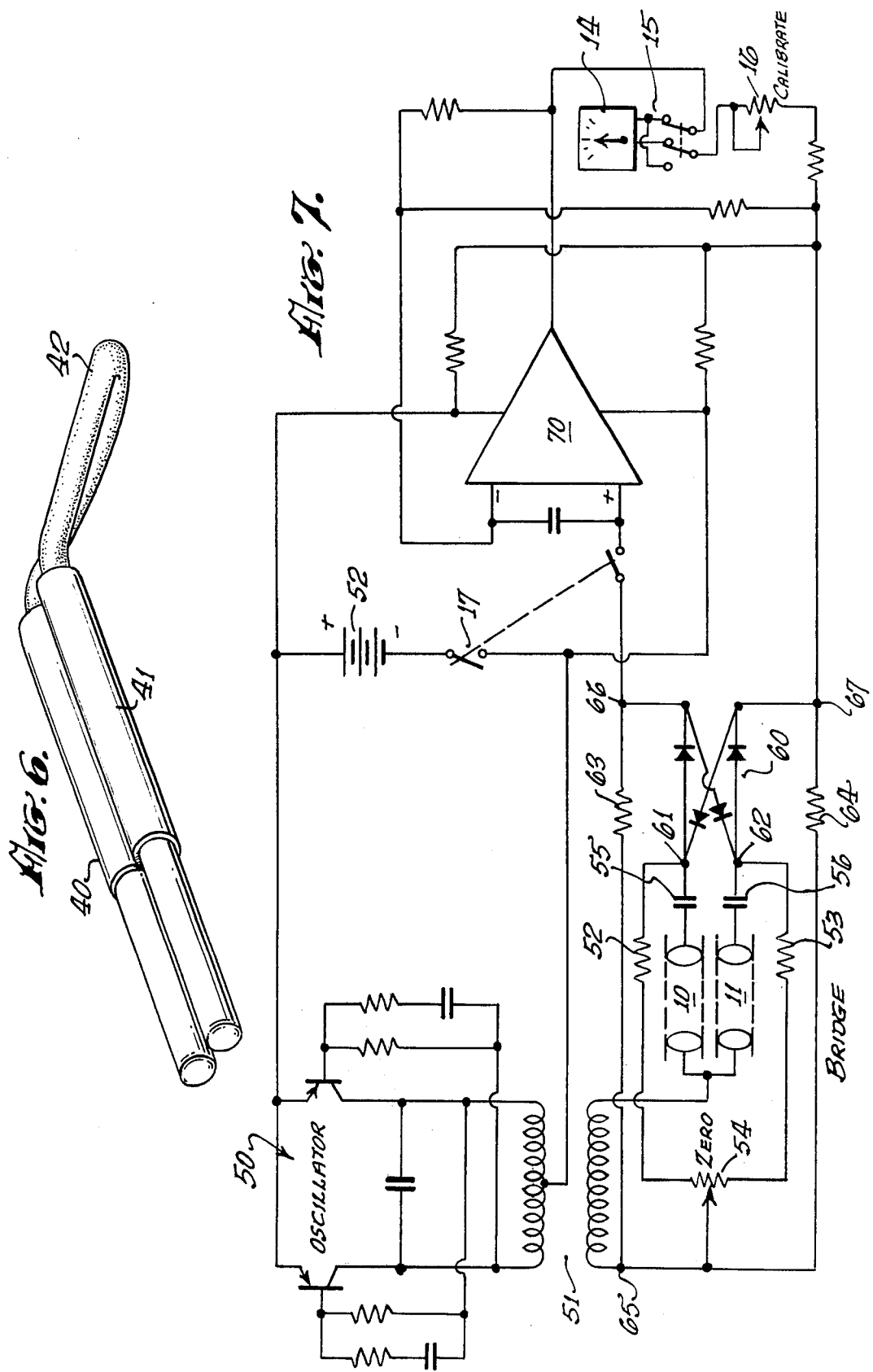

METER FOR MEASURING SYRUP RATIO IN SOFT DRINKS AND THE LIKE

BACKGROUND OF THE INVENTION

This invention relates to electrical conductivity measurements and in particular to an instrument for measuring the deviation of conductivity of a sample from that of a standard. The instrument is especially adapted for use in the soft drink industry for monitoring the syrup to water ratio of the product. The instrument is sometimes referred to as a syrup ratio meter.

The syrup to water ratio of a sample can be determined by measuring the difference in electrical conductivity of the sample and a standard of known syrup to water ratio. In the past, this measurement has been made in a laboratory using laboratory type instrumentation. A sample is brought to the laboratory, the sample and standard are put in separate relatively large conductivity cells, both cells are placed in a water bath to maintain temperature equalibrium, and the conductivity is measured for each cell. The difference in conductivity provides a measure of the difference in syrup to water ratio of the sample and standard. This type of measurement is not satisfactory because the readings are not reliable to better than ± a few percent, whereas the soft drink industry requires accuracy and repeatability of measurement in the order of ± a few tenths of a percent. At the present time, sugar type drinks are tested by specific gravity measurements and diet type drinks by chemical analysis.

It is an object of the present invention to provide a new and improved instrument and method which is suitable for use at the production line. The instrument should be simple, sensitive, stable and easy to calibrate and use.

SUMMARY OF THE INVENTION

The instrument of the present invention provides for measuring and directly indicating the conductivity ratio of two liquids. Two small conductivity cells are mounted in the instrument, preferably in side by side arrangement, with each of the cells having spaced electrodes providing an electrical path through a liquid in the cell. The cells are connected in a bridge circuit with a high frequency ac source providing the input to the bridge and with the bridge output connected through a full wave rectifier to an amplifier and meter which is calibrated to read directly in percent deviation from the standard ratio. The electrodes are positioned in the lower sections of each of the cells, with the upper sections formed of a unitary metal block for heat exchange between the liquids in the cells. Plungers are inserted into the cells for raising the liquids to the upper sections for temperature equalization and for forcing out excess liquid to provide equal amounts of liquid in each cell. The plungers are removed prior to the conductivity measurement.

The instrument is small (typically three inches by five inches by five inches overall) and self-contained, with small cells and small electrode area and with the cells enclosed, reducing the effects of body capacitance and temperature variation. The instrument is highly sensitive, providing conductivity measurements of better than one/one-hundredth of a percent and product composition measurements in tenths of a percent. The zero setting of the instrument is highly stable for standards and samples with a wide range of conductivity, permitting the zero to be set at initial manufacture without requiring adjustment by the operator.

BRIEF DESCRIPTION OF THE DRAWINGS

FIG. 1 is a perspective view of a syrup ratio meter incorporating the presently preferred embodiment of the invention;

FIG. 2 is an enlarged partial sectional view taken along the line 2—2 of FIG. 1;

FIG. 3 is a view similar to that of FIG. 2 showing the plungers of FIG. 6 is position in the cells;

FIG. 4 is a sectional view taken along the line 4—4 of FIG. 2;

FIG. 5 is an enlarged sectional view of a portion of one of the conductivity cells illustrating the electrode construction;

FIG. 6 is a perspective view of a plunger pair for use with the meter of FIG. 1; and FIG. 7 is an electrical schematic of the meter of FIG. 1.

DESCRIPTION OF THE PREFERRED EMBODIMENT

Conductivity cells 10, 11 are mounted in a tube 12 carried in a housing 13. A meter 14, a polarity switch 15, a calibration potentiometer 16, and an on-off switch 17, are also mounted on the housing 13.

The cell 10 has a lower section 20 and an upper section 21, and the cell 11 similarly has a lower section 22 and an upper section 23. The lower sections 20, 22 are identical and preferably comprise lower, middle and upper insulating tubes 26, 27, 28, with a metal ring 29 between the tubes 26, 27 and another metal ring 30 between the tubes 27, 28, with the rings 29, 30 serving as the electrodes for the cell. The preferred form of cell construction is shown in greater detail in FIG. 5, with the ring 29 cemented in position between the tubes 26, 27, with the ring and tubes having a flush inner surface. The bottom of the cells and the tube 12 is closed by a bottom member 32 which may be cemented to the tube and cells.

The upper sections 21, 23 of the conductivity cells preferably are formed from a metal block 34, typically of aluminum. A tray 35 may be carried at the upper end of the tube 12 around the block 34. A ridge 36 may be provided on the block 34 between the openings of the cells to reduce the likelihood of liquid splashing from one cell to the other.

Plungers 40, 41 are mounted on a handle 42. The plungers are designed for sliding insertion into the cells, as shown in FIG. 3. The inside dimensions of the cells and the outside dimensions of the plungers are selected such that the volume of liquid in a cell with the plunger inserted (as shown in FIG. 3) will be sufficient to provide a liquid level in the cell above the upper electrode 30 with the plunger removed (as shown in FIG. 2).

The circuit of FIG. 7 includes a transistor oscillator 50 with output transformer 51. The oscillator is powered from a battery 52 and is turned on by the switch 17. Some prior art conductivity cells have been operated with dc power and others have been operated at low frequency ac in the order of one kilohertz. Some typical dc powered cells are shown in U.S. Pat. No. 3,432,746. In the present instrument, the oscillator is operated at a relatively high frequency, typically in the range of 20 to 80 kilohertz and preferably in the range of 45 to 55 kilohertz.

The oscillator output is connected across a bridge consisting of the conductivity cells 10, 11 and resistors 52, 53. A potentiometer 54 is connected between the resistors 52, 53, with the oscillator output connected to the arm of the potentiometer for adjusting the zero setting of the circuit. Capacitors 55, 56 may be connected in series with the cells 10, 11, respectively, for decoupling the cells from the bridge output circuitry.

In the preferred embodiment illustrated, a full wave rectifier 60 is connected across the bridge output terminals 61, 62, and resistors 63, 64 are connected between the bridge input terminal 65 and rectifier output terminals 66, 67, respectively, with the rectifier functioning as a full wave detector for the bridge output and providing an input to an operational amplifier 70 which drives the meter 14 through the calibration resistor 16.

After the instrument has had the zero adjustment set and has been calibrated for a particular standard liquid, the instrument is ready for use. Zero setting and calibration will be described subsequently. In use, a quantity of a standard liquid having the desired mixture of syrup and water or an electrical conductivity equivalent to the conductivity of the desired mixture of syrup and water is poured into the cell which was used for the standard liquid during calibration. A sample is poured into the other cell. Typically, the sample is obtained by taking a container of product from the production line and pouring a portion of the contents into the cell. If the product is carbonated, it should be heated to about 120° F and shaken for about one minute to effect decarbonation as the carbon dioxide bubbles will adversely affect the accuracy of the measurement. The plungers are then inserted into the cells and pumped up and down a number of times. This plunger insertion expels excess liquid from each of the cells, and forces out bubbles that cling to the cell wall and which cause errors in measurement when present. The plunger insertion also moves a major portion of the liquids upward into the block 34. Since the block 34 is formed of metal with a high heat transfer characteristic, the temperatures of the liquids in the two cells are rapidly equalized. The plunger is then removed and the switch 17 is closed. The meter 14 will indicate any deviation in conductivity of the sample from that of the standard. Preferably, the meter 14 is a zero center meter and is calibrated in percent with the center position corresponding to 100%. If the meter deflects to 96, the operator knows that the sample is 4% low and his charts will indicate how much increase should be made in the syrup rate to obtain the desired 100 reading. Similarly, if the meter indicates 102, the operator will know how much to decrease the syrup rate to obtain the desired syrup to water ratio.

With the switch 17 closed, the oscillator 50 operates providing an ac source to the bridge. With the bridge initially balanced, any difference in conductivity of the liquids in the cells 10, 11 provide an ac differential at the terminals 61, 62. The full wave detector provides a corresponding dc differential at the terminals 66, 67. This voltage difference is connected as the input to the amplifier 70 which provides the power for driving the meter 14.

The zero potentiometer 54 is set initially by placing quantities of the same liquid in both cells, using the plungers to equalize the temperature, and then closing the switch 17. The potentiometer 54 is then adjusted to obtain a center indication for the meter 14. The instrument is now ready for use and seldom if ever requires further zero adjustment.

When in use, the instrument should be calibrated for the product being monitored. Switch 15, which has a normal and a reverse position, is set in the normal position. A quantity of the decarbonated product is placed in each of the cells, the plungers are used to equalize the temperature and remove bubbles and the switch 17 is closed. The meter should indicate 100%, i.e., no deviation from the desired ratio. Then a predetermined amount of water is added to one cell, corresponding to the sample cell. If the syrup has a higher conductivity than the water in the mixture, the instrument should now indicate less than 100%. The variable resistor 16 is adjusted to provide the specific required reading. For example, it is known that adding a specific amount of water to the cell should produce a deviation of 4%. Then the resistor 16 is adjusted to provide a reading of 96. The instrument is now ready for use as described previously.

If the syrup has a lower conductivity than the water in the mixture, the instrument will indicate greater than 100% when the calibration water is added. The polarity switch 15 is then moved to the reverse position so that the instrument will correctly indicate less than 100%. Then the resistor 16 is adjusted to produce the desired reading and the instrument is ready for use.

The switch 17 has two sets of contacts, one set at the battery 52 and one set at the input of the amplifier 70. It is preferred to have the switch constructed so that when the push button is depressed to close the switch for a reading, the battery contact set closes before the amplifier contact set closes. During the short interval between the closing of the first set and the closing of the second set, there is a large deflection of the needle of the meter 14. This provides an indication of the condition of the battery and of the position of the switch 15.

The needle will indicate above 100% when switch 15 is in the normal position and below 100% when in the reverse position. When the battery is at full strength, the needle will move a known amount; if the needle movement is less, the operator knows that the battery should be replaced.

The instrument provides for direct measurment of ratio of two components of a sample and is readily used at the production line. The instrument is inexpensive, accurate, trouble free and simple to operate and does not require any specific technique on the part of the operator. The cell construction makes the instrument easy to keep clean and free of contamination. The operation at the relatively high frequency, such as the preferred range of 45 to 55 kilohertz, permits operation of all the cells at much higher voltages and currents than in the low frequency, e.g., one kilohertz, instrument without overloading the electrodes in the cells. This means that the electrodes are far less critical while achieving high precision results.

I claim:

1. In an instrument for measuring the conductivity ratio of two liquids, the combination of:
    first and second elongate conductivity cells of substantially equal volume mounted in said instrument side-by-side with their axes substantially parallel,
    each of said cells having an upper portion with an open end and a lower portion with a closed end and having spaced electrodes in the lower portion for providing an electrical path through a liquid in the cell,
    with said upper portions of said cells formed of a single metal member and with said lower portions of each of said cells including upper and lower electrodes in the form of annular bands and an insulating tube between said bands, with said tube and bands having a flush inner surface;

means for introducing a liquid into each of said cells;

means for connecting said cells in a bridge circuit;

an ac power source connected as an input to said bridge circuit; and indicator means for indicating the output of said bridge circuit.

2. An instrument as defined in claim 1 including a pair of plungers of substantially equal size and mounted side-by-side for sliding insertion into said cells.

3. An instrument as defined in claim 1 including a full wave rectifier connected at the output of said bridge circuit with the rectifier output providing an input to said indicator means.

4. An instrument as defined in claim 3 wherein said bridge circuit includes first and second resistors connected between one terminal of said ac power source and the input to said full wave rectifier, and third and fourth resistors connected between said one terminal and the output of said full wave rectifier.

5. An instrument as defined in claim 4 including decoupling capacitors between each of said cells and said full wave rectifier input.

6. An instrument as defined in claim 5 including a potentiometer connected between said first and second resistors, with the arm of said potentiometer connected to said one terminal for zero trimming.

7. An instrument as defined in claim 1 wherein the frequency of said ac source is in the range of 20 to 80 kilohertz.

8. An instrument as defined in claim 1 wherein the frequency of said ac source is in the range of 45 to 55 kilohertz.

9. An instrument as defined in claim 1 wherein said indicator means includes:

a meter;

an amplifier for driving said meter;

a variable resistor connected in circuit with said meter for instrument calibration; and a switch for reversing the polarity at said meter.

10. A method of measuring deviation in conductivity of a sample from a standard, including the steps of:

placing a quantity of the standard in one of a pair of substantially identical conductivity cells, where each cell has a closed lower portion of an electrical insulator with spaced electrodes and both cells have a common upper portion of a metal;

placing a quantity of a sample in the other of the pair of conductivity cells;

equalizing the amounts of standard and sample in the cells and equalizing the temperature of the standard and sample in the cells by displacing the standard and sample upward by plungers inserted with the cells, to contact the metal upper portion and flow excess material out of the cells;

measuring the difference in electrical conductivity through the standard and sample; and converting the difference to a percentage of the conductivity of the standard.

11. The method of claim 10 including calibrating by the steps of:

placing the same mixture in both of the cells;

equalizing the amounts of the mixture in the cells;

equalizing the temperature of the mixture in the cells;

adding a predetermined amount of one of the components of the mixture to one of the cells;

measuring the difference in electrical conductivity through the meaterials in the two cells;

converting the difference to a percentage of the conductivity of the mixture; and adjusting the measured percentage to a predetermined figure.

12. An instrument as defined in claim 9 including;

a dc power source;

a switch having first and second contact sets with said first set closing before said second set when said switch is activated;

circuit means connecting said first contact set between said dc power source and said amplifier for providing power to the amplifier; and circuit means connecting said second contact set between the output of said bridge circuit and the input of said amplifier.

* * * * *